United States Patent
Barabolak et al.

(10) Patent No.: US 7,022,314 B2
(45) Date of Patent: Apr. 4, 2006

(54) ANTI-PLAQUE EMULSIONS AND PRODUCTS CONTAINING SAME

(75) Inventors: Roman M. Barabolak, Palos Park, IL (US); Dave L. Witkewitz, Bridgeview, IL (US)

(73) Assignee: Wm. Wrigley Jr. Company, Chicago, IL (US)

( * ) Notice: Subject to any disclaimer, the term of this patent is extended or adjusted under 35 U.S.C. 154(b) by 400 days.

(21) Appl. No.: 10/035,320

(22) Filed: Nov. 8, 2001

(65) Prior Publication Data

US 2002/0081267 A1 Jun. 27, 2002

Related U.S. Application Data

(63) Continuation of application No. 09/453,383, filed on Dec. 2, 1999, now Pat. No. 6,436,369.

(60) Provisional application No. 60/118,330, filed on Feb. 3, 1999, provisional application No. 60/112,641, filed on Dec. 17, 1998.

(51) Int. Cl.
*A61K 9/68* (2006.01)

(52) U.S. Cl. .................. 424/48; 514/835; 514/937; 426/3; 426/5; 426/6

(58) Field of Classification Search .................. 424/48, 424/440, 54, 49; 426/3–5; 514/718, 721, 514/937, 938, 941, 943
See application file for complete search history.

(56) References Cited

U.S. PATENT DOCUMENTS

| 5,032,385 | A | * | 7/1991 | Reed et al. ................. 424/49 |
| 5,108,763 | A | | 4/1992 | Chau et al. |
| 5,236,699 | A | | 8/1993 | Libin |
| 5,248,508 | A | | 9/1993 | Reed et al. |
| 5,270,061 | A | | 12/1993 | Reed et al. |
| 5,286,496 | A | | 2/1994 | Stapler et al. |
| 5,300,305 | A | | 4/1994 | Stapler et al. |
| 5,370,864 | A | | 12/1994 | Peterson et al. |
| 5,376,389 | A | | 12/1994 | Reed et al. |
| 5,380,530 | A | * | 1/1995 | Hill ............................ 424/440 |
| 5,382,424 | A | | 1/1995 | Stapler et al. |
| 5,472,685 | A | * | 12/1995 | Gaffar ......................... 424/49 |
| 5,487,902 | A | | 1/1996 | Andersen et al. |
| 5,536,511 | A | | 7/1996 | Yatka |
| 5,603,970 | A | | 2/1997 | Tyrpin et al. |
| 5,711,961 | A | | 1/1998 | Reiner et al. |
| 5,855,872 | A | | 1/1999 | Libin |
| 5,945,089 | A | | 8/1999 | Libin |
| 5,980,868 | A | | 11/1999 | Homola et al. |
| 6,290,985 | B1 | * | 9/2001 | Ream et al. ................. 424/440 |
| 6,322,806 | B1 | * | 11/2001 | Ream et al. ................. 424/440 |
| 6,350,480 | B1 | * | 2/2002 | Urnezis et al. ................ 426/5 |
| 6,355,265 | B1 | * | 3/2002 | Ream et al. ................. 424/440 |
| 6,436,369 | B1 | * | 8/2002 | Barabolak et al. ............ 424/48 |
| 6,592,912 | B1 | * | 7/2003 | Barabolak et al. ............. 426/3 |

FOREIGN PATENT DOCUMENTS

| EP | 0 696 449 A2 | | 2/1996 |
| WO | WO 95/17159 | * | 6/1995 |

OTHER PUBLICATIONS

Chemical Abstracts 119: 158564, "Destabilization of beta casein foams by competitive adsorption with the emulsifier Tween 20", Wilson et al (1993).*

Chemical Abstracts 116:39909, "Destabilization of alpha lactalbumin foams by competitive adsorption of the surfactant Tween 20", Clark et al (1991).*

Abstract Search from the United States Patent and Trademark Office dated Nov. 27, 1999; pp. 1-54.

* cited by examiner

*Primary Examiner*—Frederick Krass
(74) *Attorney, Agent, or Firm*—Bell, Boyd & Lloyd LLC

(57) ABSTRACT

Anti-plaque emulsions and methods of use are provided. The emulsion comprises a surfactant, emulsifier, and triclosan.

8 Claims, No Drawings

ANTI-PLAQUE EMULSIONS AND PRODUCTS CONTAINING SAME

This application is a continuation of U.S. Ser. No. 09/453,383, filed on Dec. 2, 1999, and now U.S. Pat. No. 6,436,369, and claims the benefit of U.S. Provisional Applications 60/112,641, filed Dec. 17, 1998, and 60/118,330, filed Feb. 3, 1999, respectively.

BACKGROUND OF THE INVENTION

The present invention relates generally to dental care products. More specifically, the present invention relates to anti-plaque products.

Of course, one of the most common maladies is dental caries. Most individuals at some time in their lives will experience dental caries. Except for the common cold, tooth decay is the most prevalent disorder.

The role of dental plaque in the formation of caries, as well as periodontal disease, is well documented. In this regard, the interaction of three factors results in dental caries: susceptible tooth surface; the proper microfora; and a suitable substrate for the microfora. Laboratory and clinical evidence points to *Streptococcus mutans* as the primary pathogen for initiating carious lesions; its virulence stems from its ability to synthesize extracellular polysaccharide. Lactic acid, a byproduct of the synthesis, contributes to tooth demineralization. Mono- and disaccharide sugars serve as the principal substrates for the process. Dental plaque—a combination of these polysaccharides, microorganisms, salivary glycoproteins, and desquamated mucosal cells—serves as a localized site of acid production. See Merck Manual, 16th Edition, pp. 2480–2481.

Even the most thorough toothbrushing and flossing fails to remove all plaque. This is especially true with respect to the plaque that is located between the teeth which can prove to cause the most damage.

Accordingly, in assisting in removing plaque, it is important to provide an oral hygiene supplement. These oral hygiene supplements include specially prepared chewing gums and oral rinses that are enhanced with antimicrobial ingredients. These compositions have proven effective. However, the level and use of the antimicrobial combinations are directly related to their effectiveness. Unfortunately, the antimicrobial ingredients have negative sensory effects such as bitterness and dental staining.

Therefore, there is a need for improved anti-plaque supplements which are delivered as emulsions to lower the effective dosage.

SUMMARY OF THE INVENTION

The present invention provides an improved anti-plaque emulsion. The improved emulsion comprises triclosan, a surfactant, and an emulsifier. The use of an emulsion improves oral contact between the teeth/plaque and the actives which allows the user to lower the triclosan levels without negatively affecting the antimicrobial benefits. Therefore, because a lower level of antimicrobial agent is utilized, the negative sensory effects of the antimicrobial agent are minimized.

To this end, in an embodiment the present invention provides an anti-plaque emulsion comprising an emulsifier, triclosan, and a surfactant.

In an embodiment, the surfactant is cetylpyridinium chloride (CPC).

In an embodiment, triclosan comprises approximately 3% to about 30% weight percent of the emulsion.

In an embodiment, the surfactant comprises approximately 0.1% to about 10% weight percent of the emulsion.

In another embodiment of the present invention, the invention provides an anti-plaque chewing gum comprising a water insoluble portion and a water soluble portion including an emulsifier, triclosan, and surfactant.

In an embodiment, the surfactant is cetylpyridinium chloride (CPC).

In an embodiment, triclosan comprises approximately 3% to about 30% weight percent of the emulsion.

In an embodiment, the surfactant comprises approximately 0.1% to about 10% weight percent of the emulsion.

In an embodiment, each piece of gum includes approximately 1 mg to about 6 mg of triclosan.

In an embodiment, the gum is in pellet form.

In a still further embodiment, a method for reducing plaque is provided comprising the step of chewing a gum comprising an emulsifier, triclosan and a surfactant.

In an embodiment of the method, the gum is chewed for at least 5 minutes.

In an embodiment of the method, the gum is chewed at least three times per day.

Accordingly, an advantage of the present invention is that it provides an improved anti-plaque emulsion.

Furthermore, an advantage of the present invention is that it provides an anti-plaque emulsion that has a reduced level of antimicrobial agent but still provides antimicrobial activity.

Moreover, an advantage of the present invention is that it provides an antimicrobial emulsion that can be used in a variety of different vehicles.

Further, an advantage of the present invention is that it provides an improved anti-plaque chewing gum.

Another advantage of the present invention is that it provides an improved anti-plaque mouthwash.

Still further, an advantage of the present invention is that it provides an improved anti-plaque product that can comprise are oral paste, gel, or powder.

Further, an advantage of the present invention is that it provides an anti-plaque product having improved taste/reduced bitterness.

Moreover, an advantage of the present invention is that it provides an anti-plaque product having improved sensory acceptability.

Additionally, an advantage of the present invention is that it provides an improved method for producing anti-plaque emulsions.

Still, an advantage of the present invention is that it provides an improved method for reducing plaque and gingivitis.

Additional features and advantages of the present invention are described herein, and will be apparent from the detailed description of the presently preferred embodiments.

DETAILED DESCRIPTION OF THE PRESENTLY PREFERRED EMBODIMENTS

The present invention provides an improved anti-plaque emulsion. It has been surprisingly found, that pursuant to the present invention, an emulsion having a low level of antimicrobial agent can be combined with a surfactant in an emulsifier to optimize the benefits of the antimicrobial agent.

The benefit to using an emulsion to carry the actives is that it enables the saliva to disperse the emulsion across the dental surfaces allowing the actives to afford a more complete oral contact with plaque covered surfaces. The emulsion is very important as it enables water insoluble actives to become beneficial in the saliva. If the actives were not in an emulsion the saliva alone would not extract the actives out of the oral hygiene product no matter how high the antimicrobial level. Since antimicrobials are effective in an emulsion, the level of the antimicrobial agent can be lowered which minimizes the negative sensory effects. At the same time the antimicrobial is maintained at a level that is sufficiently low to minimize the agents' negative sensory effects.

In this regard, it has been found that by creating an emulsion using triclosan and a surfactant, that reduced levels of triclosan can be used and an effective anti-plaque emulsion provided. This emulsion allows for improved oral contact and therefore improved antimicrobial effect is achieved. The emulsion, and its method of preparation, improve the intimate contact between the oral plaque and the plaque fighting ingredients. This combination has also been found to maximize the efficacy of the active ingredients. Moreover, the combination allows the active ingredients to be used in lower levels so that the bad taste of the ingredients as well as staining effect is minimized.

The antimicrobial material of the present invention can be used in a variety of vehicles. In this regard, anti-plaque benefits can be provided via a chewing gum, mouthwash, oral paste, gel, or powder. Any vehicle to which the delivery system of the present invention can be added can be used.

Pursuant to the present invention, reduced levels of triclosan can be used. It has been surprisingly found that higher usage levels of triclosan did not show any dental benefit. However, when a pellet gum coating consisting in part of a lower triclosan level mixed in an emulsion with a surfactant (also at a reduced level), emulsifier and flavor benefits were surprisingly evident.

The level of triclosan in an emulsion should be approximately 3% to about 30% weight percent of the emulsion, preferably approximately 7% to 20% and most preferably approximately 15%. The level of the surfactant should be approximately 0.1% to about 10% weight percent of the emulsion, preferably approximately 1.0% to about 7%, and most preferably approximately 3%.

Water is typically used in an emulsion. When CPC is used, the water is found in the aqueous CPC solution. Optionally, emulsions can also contain sweeteners.

The preferred embodiment of the invention is the use of the emulsion in a chewing gum, preferably a sugarless chewing gum (because the invention promotes dental health a non-cariogenic sweetener is preferred) and most preferably the emulsion would be included in the pellet coating of a sugarless gum. As mentioned above the emulsion can also be incorporated into other oral hygiene products.

Chewing gum generally consists of a water insoluble gum base, a water soluble portion, and flavors.

The insoluble gum base generally comprises elastomers, resins, fats and oils, softeners, and inorganic fillers. The gum base may or may not include wax. The gum base may or may not be biodegradable or include environmental release components. The insoluble gum base can constitute approximately 5 to about 95 percent, by weight, of the chewing gum, more commonly, the gum base comprises 10 to about 50 percent of the gum, and in some preferred embodiments, 20 to about 35 percent, by weight, of the chewing gum.

In an embodiment, the chewing gum base of the present invention contains about 20 to about 60 weight percent synthetic elastomer, 0 to about 30 weight percent natural elastomer, about 5 to about 55 weight percent elastomer plasticizer, about 4 to about 35 weight percent filler, about 5 to about 35 weight percent softener, and optional minor amounts (about one percent or less) of miscellaneous ingredients such as colorants, antioxidants, etc.

Synthetic elastomers may include, but are not limited to, polyisobutylene with a GPC weight average molecular weight of at out 10,000 to about 95,000, isobutylene-isoprene copolymer (butyl rubber), styrene-butadiene copolymers having styrene-butadiene ratios of about 1:3 to about 3:1, polyvinyl acetate having a GPC weight average molecular weight of about 2,000 to about 90,000, polyisoprene, polyethylene, vinyl acetate-vinyl laurate copolymer having vinyl laurate content of about 5 to about 50 percent by weight of the copolymer, and combinations thereof.

As a partial or complete substitute for conventional elastomers, biodegradable or releasable elastomers such as polyesters or food grade acids and alcohols may be used.

Preferred ranges are, for polyisobutylene, 50,000 to 80,000 GPC weight average molecular weight, for styrene-butadiene, 1:1 to 1:3 bound styrene-butadiene, for polyvinyl acetate, 10,000 to 65,000 GPC weight average molecular weight with the higher molecular weight polyvinyl acetates typically used in bubble gum base, and for vinyl acetate-vinyl laurate, vinyl laurate content of 10–45 percent.

If used, natural elastomers may include natural rubber such as smoked or liquid latex and guayule as well as natural gums such as jelutong, lechi caspi, perillo, sorva, massaranduba balata, massaranduba chocolate, nispero, rosindinha, chicle, gutta hang kang, and combinations thereof. The preferred synthetic elastomer and natural elastomer concentrations vary depending on whether the chewing gum in which the base is used is adhesive or conventional, bubble gum or regular gum, as discussed below. Preferred natural elastomers include jelutong, chicle, sorva and massaranduba balata.

If used, elastomer plasticizers may include, but are not limited to, natural rosin esters, often called estergums, such as glycerol esters of partially hydrogenated rosin, glycerol esters polymerized rosin, glycerol esters of partially dimerized rosin, glycerol esters of rosin, pentaerythritol esters of partially hydrogenated rosin, methyl and partially hydrogenated methyl esters of rosin, pentaerythritol esters of rosin; synthetics such as terpene resins derived from alpha-pinene, beta-pinene, and/or d-limonene; and any suitable combinations of the foregoing. The preferred elastomer plasticizers will also vary depending on the specific application, and on the type of elastomer which is used.

Fillers/texturizers may include magnesium and calcium carbonate, ground limestone, silicate types such as magnesium and aluminum silicate, clay, alumina, talc, titanium oxide, mono-, di- and tri-calcium phosphate, cellulose polymers, such as wood, and combinations thereof.

Softeners may include tallow, hydrogenated tallow, hydrogenated and partially hydrogenated vegetable oils, cocoa butter, glycerol triacetate, mono-, di- and triglycerides, acetylated monoglycerides, fatty acids (e.g. stearic, palmitic, oleic and linoleic acids), and combinations thereof.

Emulsifiers may include lecithin, glycerol monosterate, or other mono- and diglycerides.

Colorants and whiteners may include FD&C-type dyes and lakes, fruit and vegetable extracts, titanium dioxide, and combinations thereof.

The base may or may not include wax. An example of a wax-free gum base is disclosed in U.S. Pat. No. 5,286,500, the disclosure of which is incorporated herein by reference.

In addition to a water insoluble gum base portion, a typical chewing gum composition includes a water soluble bulk portion and one or more flavoring agents. The water soluble portion can include bulk sweeteners, high intensity sweeteners, flavoring agents, softeners, emulsifiers, colors, acidulants, fillers, antioxidants, and other components that provide desired attributes.

The softeners, which are also known as plasticizers and plasticizing agents, generally constitute between approximately 0.5 to about 15% by weight of the chewing gum. The softeners may include glycerin, and combinations thereof. Aqueous sweetener solutions such as those containing sorbitol, hydrogenated starch hydrolysates, corn syrup and combinations thereof, may also be used as softeners and binding agents in chewing gum.

An emulsifier such as lecithin may be added to the gum.

Bulk sweeteners include both sugar and sugarless components. Bulk sweeteners typically constitute 5 to about 95% by weight of the chewing gum, more typically, 20 to 80% by weight, and more commonly, 30 to 60% by weight of the gum.

Sugar sweeteners generally include saccharide-containing components commonly known in the chewing gum art, including, but not limited to, sucrose, dextrose, maltose, dextrin, dried invert sugar, fructose, galactose, corn syrup solids, and the like, alone or in combination.

Sorbitol can be used as a sugarless sweetener. Additionally, sugarless sweeteners can include, but are not limited to, other sugar alcohols such as mannitol, hydrogenated isomoltulose (palatinit), xylitol, hydrogenated starch hydrolysates, maltitol, lactitol and the like, alone or in combination.

High intensity artificial sweeteners can also be used in combination with the above. Preferred sweeteners include, but are not limited to sucralose, aspartame, salts of acesulfame, alitame, saccharin and its salts, cyclamic acid and its salts, glycyrrhizin, dihydrochalcones, thaumatin, monellin, and the like, alone or in combination. In order to provide longer lasting sweetness and flavor perception, it may be desirable to encapsulate or otherwise control the release of at least a portion of the artificial sweetener. Such techniques as wet granulation, wax granulation, spray drying, spray chilling, fluid bed coating, coacervation, and fiber extension may be used to achieve the desired release characteristics.

Usage level of the artificial sweetener will vary greatly and will depend on such factors as potency of the sweetener, rate of release, desired sweetness of the product, level and type of flavor used and cost considerations. Thus, the active level of artificial sweetener may vary from 0.02 to about 8%. When carriers used for encapsulation are included, the usage level of the encapsulated sweetener will be proportionately higher.

Combinations of sugar and/or sugarless sweeteners may be used in chewing gum. Additionally, the softener may also provide additional sweetness such as with aqueous sugar or alditol solutions.

If a low calorie gum is desired, a low caloric bulking agent can be used. Example of low caloric bulking agents include: polydextrose; Raftilose, Raftilin; Fructooligosaccharides (NUTRAFLORA); Palatinose oligosaccharide; Guar Gum Hydrolysate (SUN FIBER); or indigestible dextrin (FIBERSOL). However, other low calorie bulking agents can be used.

A variety of flavoring agents can be used. The flavor can be used in amounts of approximately 0.1 to about 15 weight percent of the gum, and preferably, about 0.2 to about 5%. Flavoring agents may include essential oils, synthetic flavors or emulsions thereof including, but not limited to, oils derived from plants and fruits such as citrus oils, fruit essences, peppermint oil, spearmint oil, other mint oils, clove oil, oil of wintergreen, anise and the like. Artificial flavoring agents and components may also be used. Natural and artificial flavoring agents may be combined in any sensorially acceptable fashion.

The present invention, it is believed, can be used with a variety of processes for manufacturing chewing gum.

Chewing gum is generally manufactured by sequentially adding the various chewing gum ingredients to commercially available mixers known in the art. After the ingredients have been thoroughly mixed, the chewing gum mass is discharged from the mixer and shaped into the desired form, such as by rolling into sheets and cutting into sticks, extruding into chunks, or casting into pellets.

Generally, the ingredients are mixed by first melting the gum base and adding it to the running mixer. The gum base may alternatively be melted in the mixer. Color and emulsifiers can be added at this time.

A chewing gum softener such as glycerin can be added next along with part of the bulk portion. Further parts of the bulk portion may then be added to the mixer. Flavoring agents are typically added with the final part of the bulk portion. The entire mixing process typically takes from five to fifteen minutes, although longer mixing times are sometimes required.

By way of example, and not limitation, examples of embodiments of the present invention will now be given:

A chewing gum composition using the present invention was prepared as follows:

EXAMPLE 1

| PELLET GUM CENTER | |
| --- | --- |
| INGREDIENT | PERCENT |
| Sorbitol & Liquid Sorbitol | 47.00% |
| Base | 32.00% |
| Calcium Carbonate | 15.00% |
| Flavor | 4.38% |
| Glycerin | 0.75% |
| Encapsulated High Intensity Sweeteners | 0.87% |

The ingredients were mixed conventionally and formed into 1 gram pillow shaped pellets. The following coating was then appled to the pellets at a level to yield a final piece size of 1.52 grams.

EXAMPLE 2

| PELLET GUM COATING (dry composition) | |
| --- | --- |
| INGREDIENT | PERCENT |
| Palatinit Course | 57.83% |
| Palatinit Fine Powder | 30.40% |
| Gum Talha | 6.20% |
| Color | 1.44% |
| Encapsulated High Intensity Sweeteners | 0.53% |
| Flavor | 2.02% |
| Triclosan | 0.50% |
| CPC solution (25%) | 0.40% |

-continued

PELLET GUM COATING (dry composition)

| INGREDIENT | PERCENT |
|---|---|
| Hydroxylated Lecithin | 0.40% |
| Talc Powder | 0.16% |
| Carnauba Wax | 0.12% |

Coarse Palatinit and Gum Talha were dissolved in water. Palatinit fine powder, color, and encapsulated high intensity sweetness were then dispersed into the solution to make a syrup suspension (73% solids), which was used to pan coat the gum centers by a conventional method.

The Emulsion was made in a multi-step process. First the flavor components were blended and warmed until all were dissolved. Second triclosan was dissolved into flavor. Third hydroxylated lecithin was mixed into flavor/triclosan. Separately the CPC and water were mixed very slowly—agitation was avoided as it will cause foaming and prolong the dissolution of the CPC. When CPC was dissolved in the water it was combined with other ingredients and agitated well during this combination. When the emulsion was milky white it was added to the shell coating on the gum pellets by conventional pan coating methods after syrup application was completed. Please note water is typically a required ingredient in an emulsion—in this case it is found in the CPC aqueous solution. Flavor was used as a solvent for the triclosan.

The remaining pellet coating ingredients, talc and carnauba wax, were applied separately after the pellets had dried to act as a polishing ingredient. The finished, coated pellets are referred to as Example 3.

By way of example, this invention can be separated into two unique embodiments: 1) the gum itself which delivers an improved anti-plaque composition; and 2) the dosage procedure which outlines the optimum number of pellets to be chewed to receive a significant level of change in plaque buildup (as illustrated in the Human Clinical Study set forth below).

In a first embodiment, the preferred vehicle is a coated chewing gum with the active emulsion in the coating. (In testing, addition of non-emulsified actives to the gum failed to provide a benefit, probably due to solubilization of triclosan into the hydrophobic gum base.) Other vehicles as described above may also be employed. When optimizing the practice of the current invention, the coating carries the Triclosan and the surfactant and the ratio of these ingredients in the coating emulsion dictates the successfulness of the resulting product's ability to combat plaque.

In an embodiment, the dosage will comprise two pellets. The triclosan level (released in 2 pellets of gum/one dosage) in its broadest usage should be approximately 1 mg to about 12 mg. Preferably the dosage is approximately 3 mg to about 8 mg, and most preferably approximately 5 mg to about 6 mg.

The surfactant will be added at a level sufficient to enhance antimicrobial effectiveness. To this end the surfactant should comprise approximately 5% to about 80% of the triclosan level, preferably the surfactant would be approximately 10% to about 40%, and most preferably the surfactant level would be approximately 15% to about 30% of the triclosan level.

The preferred surfactant is cetyl pyridinium chloride (CPC). However, other ionic and non-ionic surfactants may also be employed.

In a second embodiment, the present invention contemplates a method of reducing plaque accumulation on teeth comprising the steps of providing a gum composition as described above. The gum is chewed for a time sufficient to derive anti-plaque benefits from it. The treatment is repeated a sufficient number of times per day to reduce plaque accumulation.

Preferably, the gum is chewed for at least 5 minutes, more preferably at least 10 minutes and most preferably at least 20 minutes. Preferably, the treatment is administered at least three times per day, more preferably five times per day, and most preferably seven times per day.

Experimental Results

Human clinical studies were performed to compare the dose-response of experimental chewing gums containing anti-plaque agents. In general, chewing gum has been advocated as a possible mechanical aid for cleaning the teeth. Because gum chewing is pleasurable, people normally chew for longer periods of time than they spend brushing their teeth. Additionally, gum chewing may hit areas missed in brushing. Further chewing gum can replace brushing when tooth brushing is not possible or convenient.

Previous human clinical studies have shown that conventional sugarless gum is capable of removing small, but significant, amounts of plaque from the teeth. It may be possible to augment this plaque cleaning effect by the addition of certain anti-plaque agents (such as Chlorhexidine, triclosan, and cetylpyridinium chloride (CPC)).

Clinical tests (two day cross-over plaque clinical studies) were run to determine the effectiveness of several gum compositions for anti-plaque activity. In the first study a gum with a coating comprising 5 mg CPC in two pellets (EXAMPLE 4) was compared to a gum with a coating comprising 11 mg triclosan in two pellets (EXAMPLE 5) and a placebo control. After the subjects had an initial cleaning, the gums were chewed three times per day (10 minute chew time) for a period of 2 days. The subjects were then evaluated for plaque in dental examinations by two independent dentists using different plaque indices. The results are reported in Table 1.

Both experimental samples had objectionable bitterness which would probably preclude regular use.

A second clinical test was conducted using a chewing gum formulated with 3 mg CPC in the center (EXAMPLE 6) in an effort to improve sensory acceptability. In this test no reduction in plaque was observed, but the gum was palatable. (See Table 1).

In the third study, the gum of EXAMPLE 3 was compared with a placebo control. In this study the gums were chewed five times per day. The result is presented in Table 1.

TABLE 1

|  | Example 4 (5 mg CPC in coating) Comparative | Example 5 (11 mg triclosan in coating) Comparative | Example 6 (3 mg CPC in center) Comparative | Example 3 (5 mg triclosan 1 mg CPC in coating) Inventive |
|---|---|---|---|---|
| Doses per day (2 pellets per dose) | 3 | 3 | 3 | 5 |
| Total active per day | 15 mg CPC | 33 mg triclosan | 9 mg CPC | 25 mg triclosan 5 mg CPC |
| % reduction in | 15% | 9% | 0% | 12% |

TABLE 1-continued

|  | Example 4 (5 mg CPC in coating) Comparative | Example 5 (11 mg triclosan in coating) Comparative | Example 6 (3 mg CPC in center) Comparative | Example 3 (5 mg triclosan 1 mg CPC in coating) Inventive |
|---|---|---|---|---|
| plaque vs control Significance (p) | <0.05% | NS | NS | <0.05% |
| Sensory comment | unacceptable | unacceptable | acceptable | acceptable |

It was concluded that the inventive gum (EXAMPLE 3) was effective at reducing plaque despite lower levels and lower total dose of active ingredients. Furthermore, the gum was pleasant to chew thereby increasing the likelihood of regular use.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

We claim:

1. An anti-plaque chewing gum comprising:
   a water insoluble portion; and
   a water soluble portion including an aqueous emulsion comprising a mixture of water, an emulsifier, triclosan, and cetylpyridinium chloride.

2. The anti-plaque chewing gum of claim 1 including a solvent for the triclosan.

3. The anti-plaque chewing gum of claim 2 wherein the solvent is a flavor.

4. The anti-plaque chewing gum of claim 1 wherein triclosan comprises approximately 3% to about 30% weight percent of the emulsion.

5. The anti-plaque chewing gum of claim 1 wherein the cetylpyridinium chloride comprises approximately 0.1% to about 10% weight percent of the emulsion.

6. The anti-plaque chewing gum of claim 1 wherein said gum comprises pieces, and each piece of gum includes approximately 1 mg to about 6 mg of triclosan.

7. The anti-plaque chewing gum of claim 1 wherein the gum is in pellet form.

8. The anti-plaque chewing gum of claim 7 wherein the emulsifier, triclosan and cetylpyridinium chloride define, in part, a coating of the pellet.

* * * * *